(12) United States Patent
Terentiev et al.

(10) Patent No.: US 8,708,319 B2
(45) Date of Patent: Apr. 29, 2014

(54) MIXING BAG WITH INTEGRAL SPARGER AND SENSOR RECEIVER

(75) Inventors: Alexandre N. Terentiev, Lexington, KY (US); Sergey Terentiev, Chaska, MN (US)

(73) Assignee: Pall Technology UK Limited, Portsmouth (GB)

( * ) Notice: Subject to any disclaimer, the term of this patent is extended or adjusted under 35 U.S.C. 154(b) by 0 days.

(21) Appl. No.: 13/599,652

(22) Filed: Aug. 30, 2012

(65) Prior Publication Data

US 2013/0171723 A1 Jul. 4, 2013

Related U.S. Application Data

(60) Continuation of application No. 13/405,609, filed on Feb. 27, 2012, now Pat. No. 8,550,439, and a continuation of application No. 12/761,111, filed on Apr. 15, 2010, now Pat. No. 8,123,199, and a continuation of application No. 12/341,478, filed on Dec. 22, 2008, now Pat. No. 7,992,846, and a division of application No. 11/304,417, filed on Dec. 15, 2005, now Pat. No. 7,469,884, and a continuation of application No. PCT/US2005/000464, filed on Jan. 7, 2005.

(60) Provisional application No. 60/599,960, filed on Aug. 9, 2004, provisional application No. 60/535,031, filed on Jan. 7, 2004.

(51) Int. Cl.
 *B01F 3/04* (2006.01)

(52) U.S. Cl.
 USPC ............... 261/121.1; 356/440; 435/288.7

(58) Field of Classification Search
 USPC .......... 261/121.1, 122.1, 122.2; 73/52, 866.5; 356/239.6, 246, 440; 435/288.7
 See application file for complete search history.

(56) References Cited

U.S. PATENT DOCUMENTS

| | | | |
|---|---|---|---|
| 4,649,114 A | 3/1987 | Miltenburger et al. | |
| 5,246,855 A | 9/1993 | Katinger et al. | |
| 5,501,971 A | 3/1996 | Freedman et al. | |
| 7,674,254 B2 * | 3/2010 | Baumfalk et al. | 604/533 |
| 7,824,902 B2 * | 11/2010 | Selker et al. | 435/288.7 |
| 7,992,846 B2 * | 8/2011 | Terentiev et al. | 261/122.1 |
| 8,123,199 B2 * | 2/2012 | Terentiev et al. | 261/93 |
| 8,550,439 B2 * | 10/2013 | Terentiev et al. | 261/121.1 |
| 2002/0028478 A1 | 3/2002 | Lehmann | |
| 2003/0070942 A1 | 4/2003 | Ossart | |
| 2007/0159920 A1 | 7/2007 | Baumfalk et al. | |
| 2008/0032389 A1 | 2/2008 | Selker et al. | |
| 2011/0124035 A1 * | 5/2011 | Broadley et al. | 435/29 |
| 2012/0072028 A1 * | 3/2012 | West | 700/266 |

FOREIGN PATENT DOCUMENTS

| | | |
|---|---|---|
| DE | 102006001623 A1 | 7/2007 |
| GB | 2177801 A | 1/1987 |
| JP | 3010677 A | 1/1991 |
| JP | 03010677 A1 | 1/1991 |
| WO | 2007039600 A1 | 4/2007 |
| WO | 2007134267 A2 | 11/2007 |
| WO | 2010010313 A2 | 1/2010 |

* cited by examiner

*Primary Examiner* — Charles Bushey
(74) *Attorney, Agent, or Firm* — King & Schickli, PLLC

(57) ABSTRACT

A mixing bag for use in bioprocessing in which a fluid is received and agitated using an internal fluid-agitating element driven by an external motive device is disclosed. The bag may include an integral sparger and sensor receiver. Related methods are also disclosed.

26 Claims, 12 Drawing Sheets

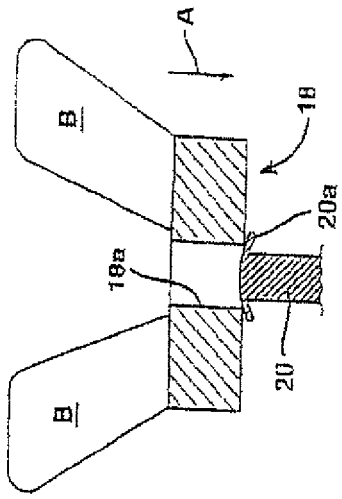
FIG. 1B
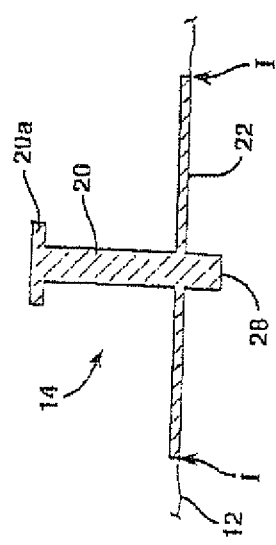
FIG. 1A
FIG. 1C

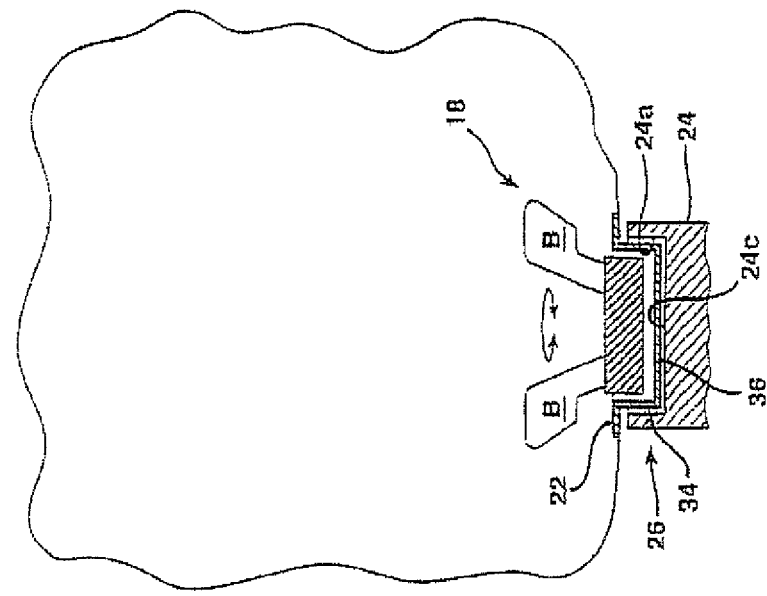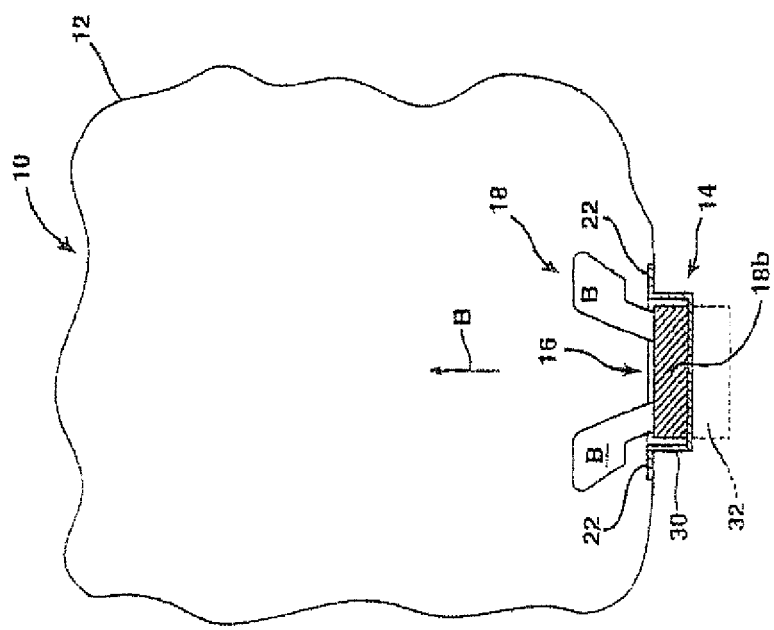

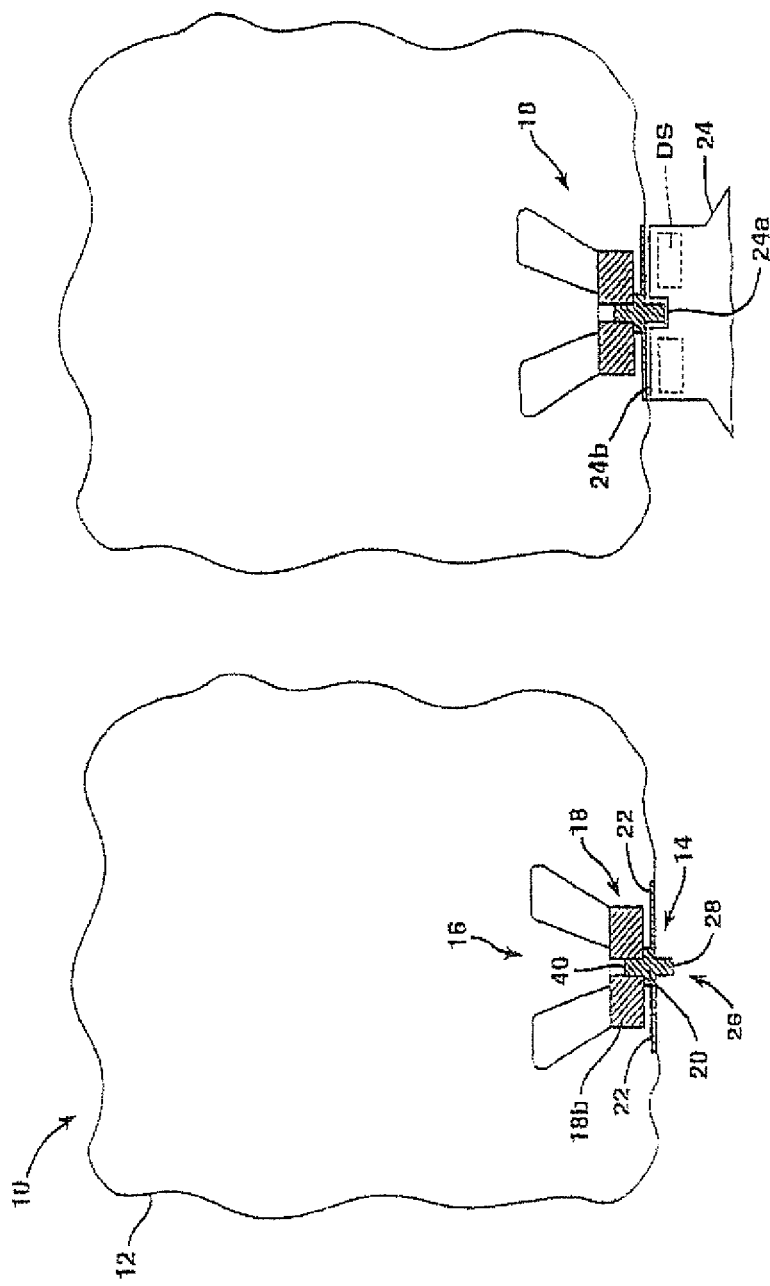

MIXING BAG WITH INTEGRAL SPARGER AND SENSOR RECEIVER

This application is a continuation of U.S. patent application Ser. No. 13/405,609, now U.S. Pat. No. 8,550,439 which is a continuation of U.S. patent application Ser. No. 12/761,111, now U.S. Pat. No. 8,123,199B2, which is a continuation of Ser. No. 12/341,478, now U.S. Pat. No. 7,992,846B2, which is a divisional of U.S. patent application Ser. No. 11/304,417, now U.S. Pat. No. 7,469,884B2, which is a continuation of international application Ser. No. PCT/US05/00464, which claims the benefit of U.S. Provisional Patent Application Ser. No. 60/535,031, filed Jan. 7, 2004, and U.S. Provisional Patent Application Ser. No. 60/599,960, filed Aug. 9, 2004, the disclosures of which are all incorporated herein by reference.

TECHNICAL FIELD

The present invention relates generally to vessels in which fluids are agitated and, more particularly, to a mixing bag.

BACKGROUND OF THE INVENTION

Most pharmaceutical solutions and suspensions manufactured on an industrial scale require highly controlled, thorough mixing to achieve a satisfactory yield and ensure a uniform distribution of ingredients in the final product. Agitator tanks are frequently used to complete the mixing process, but a better degree of mixing is normally achieved by using a mechanical stirrer or impeller (e.g., a set of mixing blades attached to a metal rod). Typically, the mechanical stirrer or impeller is simply lowered into the fluid through an opening in the top of the vessel and rotated by an external motor to create the desired mixing action.

One significant limitation or shortcoming of such an arrangement is the danger of contamination or leakage during mixing. The rod carrying the mixing blades or impeller is typically introduced into the vessel through a dynamic seal or bearing. This opening provides an opportunity for bacteria or other contaminants to enter, which of course can lead to the degradation of the product. A corresponding danger of environmental contamination exists in applications involving hazardous or toxic fluids, or suspensions of pathogenic organisms, since dynamic seals or bearings are prone to leakage. Cleanup and sterilization are also made difficult by the dynamic bearings or seals, since these structures typically include folds and crevices that are difficult to reach. Since these problems are faced by all manufacturers of sterile solutions, pharmaceuticals, or the like, the U.S. Food and Drug Administration (FDA) has consequently promulgated strict processing requirements for such fluids, and especially those slated for intravenous use.

In an effort to overcome these problems, the recent trend in the biotechnology industry is to use disposable plastic bags for a number of bioprocessing steps. Pre-sterilized disposable plastic bags eliminate the need for cleaning, sterilization and validation of the containers after each bioprocessing batch. Their use thus results in substantial saving in the cost of manufacturing of biopharmaceuticals.

Typically, one of the bioprocessing steps used in such manufacturing is growing cell culture(s) in the container, sometimes called a "bioreactor." A traditional bioreactor is a sterile vessel made out of stainless steel or glass with highly controlled environmental parameters including temperature, pH, oxygen concentration, $CO_2$ concentration, which are monitored by permanent sensors built into the rigid vessel.

During the cell growth process, the fluid in the bioreactor must also be agitated in order to maintain uniform distribution of temperature, gases and nutrients. As noted above, agitation is typically provided by an impeller with the blades housed on the shaft connected to an external motor and introduced inside the bioreactor through the dynamic seal in an effort to maintain sterility.

For normal cell growth certain concentration of dissolved oxygen must be maintained. Also, controlled introduction of other gases like carbon dioxide and nitrogen are normally necessary during bioreactor runs. The most efficient way of introducing gases in to bioreactor fluid is sparging, which involves forming small bubbles in the fluid. Such bubbles have large surface to volume ratio and thus can be dissolved more quickly than large size bubbles.

Traditionally, porous solid materials (like titanium) associated with the rigid bioreactor provide sparging. Alternatively, metal sparging rings with small pre-drilled holes are permanently affixed in some rigid bioreactors. In both cases, the bioreactors are not readily disposable and thus must be cleaned and sterilized before reuse for bioprocessing.

In traditional rigid vessel bioreactor, the impeller, sparger, gas, temperature and pH sensors are reusable components that must be cleaned and sterilized after each batch. In the case of disposable bag bioreactors, it is desirable that all the fluid touching components are only used once. This presents the challenging task of providing inexpensive fluid-touching components that can be discarded along with the bag after use.

Another challenge is positioning the components of the bioreactor on the flexible bag. Unlike a rigid vessel, a bioreactor plastic bag (which is basically thin film) has no shape or structural rigidity. Traditionally, bioreactor components like impeller shafts, spargers, sensors are housed on the rigid walls of the vessel by means of threads, bolts or clamps. Obviously, this method of component attachment does not work for plastic bags.

Thus, a need is identified for an improved manner of providing a mixing bag or flexible vessel with an integrated sparger and sensor(s). The improvement provided by the invention would be easy to implement using existing manufacturing techniques and without significant additional expense. Overall, a substantial gain in efficiency and ease of use would be realized as a result of the improvement, and would greatly expand the potential applications for which advanced mixing systems may be used, including bioprocessing.

SUMMARY OF THE INVENTION

An apparatus for receiving a fluid and sensing a characteristic thereof using a sensor element for the fluid, comprising a vessel having a flexible sidewall at least partially defining an interior compartment, a portion of the vessel formed by the flexible sidewall having no predetermined shape and capable of assuming a particular shape based on the presence of the fluid in the interior compartment, and a receiver connected to the vessel for receiving the sensor element.

In one embodiment, a tube is provided for supporting the sensor element, the tube being adapted for positioning in the receiver. The tube is positioned in contact with the fluid, and is adapted for positioning in the receiver in contact with the fluid when present. A fluid-impervious seal also connects the receiver to the vessel. The receiver includes a portion adapted for connecting with a tube, such as a barb arranged on a tubular portion of the receiver. The receiver also includes a tubular portion external to the vessel, which may include a passage for receiving the sensor element.

Another aspect of the disclosure relates to an apparatus comprising a flexible vessel having an interior space bounded by a surface, the flexible vessel being selectively movable between an extended position wherein a first portion and an opposing second portion are spaced apart and a collapsed position wherein the first portion and the opposing second portion are moved closer together relative to the extended position, and a connector secured to the second end of the flexible vessel, the connector having an opening extending therethrough that communicates with the space of the flexible vessel, and an elongated probe having a first end and an opposing second end, the second end of the probe being positioned within the interior space of the flexible vessel, the second end of the probe being configured to pass through the opening of the connector, and a sealing layer for sealing opening of the connector.

In one embodiment, the vessel comprises a bag, and the sealing layer comprises a flexible plastic material. The probe carries a sensor element for contacting the fluid. The connector is connected to the flexible vessel, and there may be an adhesive for securing the sealing layer to the connector. The second end of the probe is positioned within the interior space, and the space may be sealed by the probe.

Another aspect of this disclosure relates to an apparatus comprising a flexible vessel including a passage, said vessel having an interior surface extending between a first end and an opposing second end, the flexible vessel being selectively movable between an extended position wherein the first end and the opposing second end are spaced apart and a collapsed position wherein the first end and the opposing second end are moved closer together relative to the extended position; a connector secured to the second end of the flexible vessel, the connector having an opening extending therethrough that communicates with the interior compartment of the flexible vessel, and an elongated tube having a first end and an opposing second end, the second end of the tube being positioned within the interior compartment of the flexible vessel, the second end of the tube being configured to pass through the opening of the connector, said tube carrying at least one sensor element.

The apparatus may include a flexible plastic material for forming a seal between the tube and the connector. The vessel may comprise a bag.

BRIEF DESCRIPTION OF THE DRAWINGS

FIGS. 1, 1a, 1b and 1c are partially schematic, partially cross-sectional side views of one embodiment of a vessel in the form of a bag having a flexible portion and a rigid portion;

FIG. 3a is partially schematic, partially cross-sectional side view showing another embodiment of the vessel, including a hat or cap-shaped rigid portion having a cavity facing inwardly;

FIG. 3b is a side view similar to FIG. 3a;

FIG. 4b is a side view similar to FIG. 4a;

FIGS. 5a, 5b, 6a, 6b, and 7a, 7b are each partially schematic, partially cross-sectional side views of a vessel with a rigid portion for aligning a fluid-agitating element with a external structure, wherein the fluid-agitating element is directly supported by a slide bearing;

DETAILED DESCRIPTION OF THE INVENTION

Figure 1:
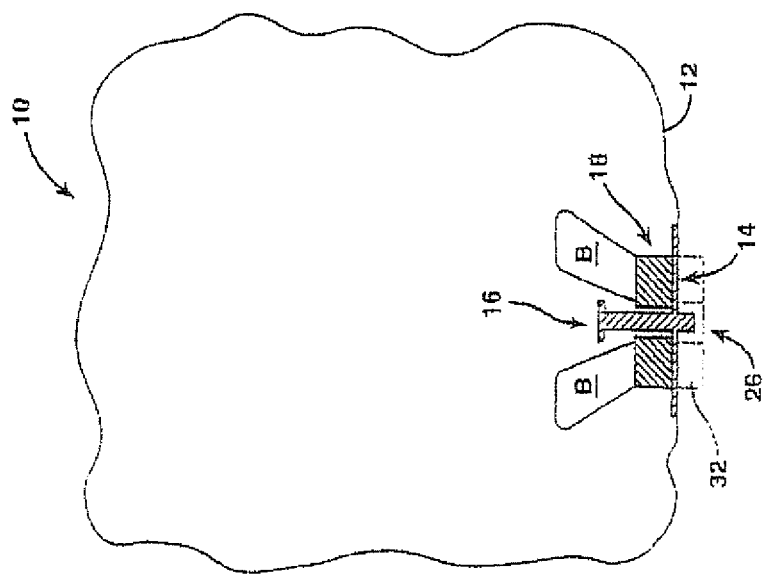

Reference is now made to FIG. 1, which discloses one embodiment of the vessel of the present invention in the form of a bag 10. In this embodiment, the bag 10 includes a body having a flexible or non-rigid portion 12, which is illustrated schematically, and a rigid or stiff portion 14, which is shown in cross-section. However, as outlined further in the description that follows, the use of the many of the present inventive concepts disclosed herein with vessels that are completely rigid is also possible.

The bag 10 may be hermetically sealed and may have one or more openings or fittings (not shown) for introducing or recovering a fluid. Alternatively, the bag 10 may be unsealed or open-ended. The particular geometry of the bag 10 employed normally depends on the application and is not considered critical to the invention. For example, in the case of a sterile fluid, a hermetically sealed, pre-sterilized bag with an aseptic fitting might be desirable; whereas, in the case where sterility is not important, an open-ended or unsealed bag might be suitable. The main important point is that the bag 10 is capable of receiving and at least temporarily holding a fluid (which is used herein to denote any substance capable of flowing, as may include liquids, liquid suspensions, gases, gaseous suspensions, or the like, without limitation).

The rigid portion 14 includes a first receiver 16 for receiving and holding a fluid-agitating element 18 at a home location (or expected position), when positioned in the bag 10. It is noted that "holding" as used herein defines both the case where the fluid-agitating element 18 is directly held and supported by the first receiver 16 (see below) against any significant side-to-side movement (save tolerances), as well as where the first receiver 16 merely limits the fluid-agitating element to a certain degree of side-to-side movement within the bag 10. In this embodiment, an opening 18a is provided in the fluid-agitating element 18 and the first receiver 16 is a post 20 projecting toward the interior of the bag 10 (see FIGS. 1a and 1b). The post 20 is sized for receiving the fluid-agitating element 18 by extending through the opening 18a formed in the body 18b thereof (which is depicted as being annular, but not necessarily circular in cross-section). As illustrated in FIG. 1, it is preferable that the size of the opening 18a is such that the fluid-agitating element 18 may freely rotate and move in the axial direction along the post 20 without contacting the outer surface thereof. Despite this freedom of movement, the post 20 serving as the first receiver 16 is still considered to hold, confine, or keep the fluid-agitating element 18 at a home location or expected position within the vessel 10 by contacting the surface adjacent to the opening 18a as a result of any side-to-side movement (the boundaries of which are defined by the dimensions of the opening).

The flexible portion 12 of the bag 10 may be made from one or more sheets of thin (e.g., having a thickness of between 0.1 and 0.2 millimeters) polyethylene film secured together to define a compartment for receiving the fluid. Preferably, the film used is clear or translucent, although the use of opaque or colored films is also possible. The rigid portion 14 including the post 20 may be formed of materials, such as high density polyethylene (HDPE), ultrahigh molecular weight (UHMW) polyethylene, or like materials. Of course, these materials do have some inherent flexibility when used to form relatively thin components or when a moderate amount of bending force is applied thereto. Despite this flexibility, the rigid portion 14 is distinguished from the flexible portion 12, in that it generally maintains its shape under the weight of fluid introduced in the bag 10.

Optionally, the post 20 may include a portion 20a for capturing the fluid-agitating element 18 and assisting in holding it thereon. The portion 20a is preferably oversized and forms the head or end of the post 20. By "oversized," it is meant that at least one dimension (length, width, diameter) of this portion 20a of the post 20 is greater than the corresponding dimension of the opening 18a in the fluid-agitating element 18. For example, the portion 20a is shown in FIG. 1 as being disc-shaped, such that it provides the head end of the post 20 with a generally T-shaped cross section. To prevent interference with the levitation and rotation of the fluid-agitating element 18, the oversized portion 20a is strategically positioned at a certain distance along the post 20. In the case where it is oversized, the post 20 may be removably attached to the rigid portion 14 through the opening 18a in the fluid-agitating element 18 (such as by providing a threaded bore in the rigid portion for receiving a threaded end of the post, or as shown in FIG. 1c, a bore 14a having a groove 14b for establishing a snap-fit engagement with a corresponding projection 20b on a tapered end portion 20c of the post). In the case where the post 20 is unitarily formed with the rigid portion 14 and includes an oversized head portion 20a, this portion should be sufficiently thin such that it flexes or temporarily deforms to allow the fluid-agitating element 18 to pass initially (see FIG. 1b and note action arrow A, which demonstrates the direction of force for deforming the oversized head 20a such that it passes through the opening 18a).

Alternatively, this portion 20a of the post 20 need not be oversized, as defined above, but instead may simply be sufficiently close in size to that of the opening 18a such that the fluid-agitating element 18 must be precisely aligned and register with the post 20 in order to be received or removed. In any case, it is again important to note that the fluid-agitating element 18 is held in place in the vicinity of the post 20, but remains free of direct attachment. In other words, while the first receiver 16 (post 20) confines or holds the fluid-agitating element 18 at a home location or expected position within the bag 10, it is still free to move side-to-side to some degree (which in this case is defined by the size of the opening 18a), and to move along the first receiver 16 in the axial direction (vertical, in the embodiment shown in FIG. 1), as is necessary for levitation.

As perhaps best shown in FIG. 1a, the rigid portion 14 in this embodiment further includes a substantially planar peripheral flange 22. The flange 22 may be any shape or size, and is preferably attached or connected directly to the bag 10 at the interface I between the two structures (which may be created by overlapping the material forming the flexible portion 12 of the bag on an inside or outside surface of the flange 22 to form an overlapping joint, or possibly in some cases by forming a butt joint). In the case where the bag 10 and flange 22 are fabricated of compatible plastic materials, the connection may be made using well-known techniques, such as ultrasonic or thermal welding (heat or laser) at the interface to form a seal (which is at least liquid-impervious and preferably hermetic). Alternatively, other means of connection (e.g., adhesives), may be used at the interface I, although this is obviously less preferred in view of the desirability in most cases for the more reliable, leak-proof seal afforded using welding techniques. In either case, the judicious use of inert sealants may be made along the joint thus formed to ensure that a leak-proof, hermetic seal results. As discussed further below, the need for such an interface may be altogether eliminated by simply affixing the rigid portion 14 to an inside or outside surface of the bag 10.

As should be appreciated, the bag 10 shown in FIG. 1 may be manufactured as described above, with the fluid-agitating element 18 received on the post 20 (which may be accomplished using the techniques shown in FIGS. 1b and 1c). The empty bag 10 may then be sealed and folded for shipping, with the fluid-agitating element 18 held at the home location by the post 20. Holding in the axial direction (i.e., the vertical direction in FIG. 1) may be accomplished by folding the bag 10 over the post 20, or by providing the portion 20a that is oversized or very close in size to the opening 18a in the fluid-agitating element 18.

When ready for use, the bag 10 is then unfolded. It may then be placed in a rigid or semi-rigid support structure, such as a container C, partially open along at least one end such that at least the rigid portion 14 remains exposed (see FIG. 2). Fluid F may then be introduced into the bag 10, such as through an opening or fitting (which may be a sterile or aseptic fitting, in the case where the bag 10 is pre-sterilized or otherwise used in a sterile environment). As should be appreciated, in view of the flexible or non-rigid nature of the bag 10, it will generally occupy any adjacent space provided in an adjacent support structure or container C when a fluid F (liquid or gas under pressure) is introduced therein (see FIG. 2).

Figure 2:
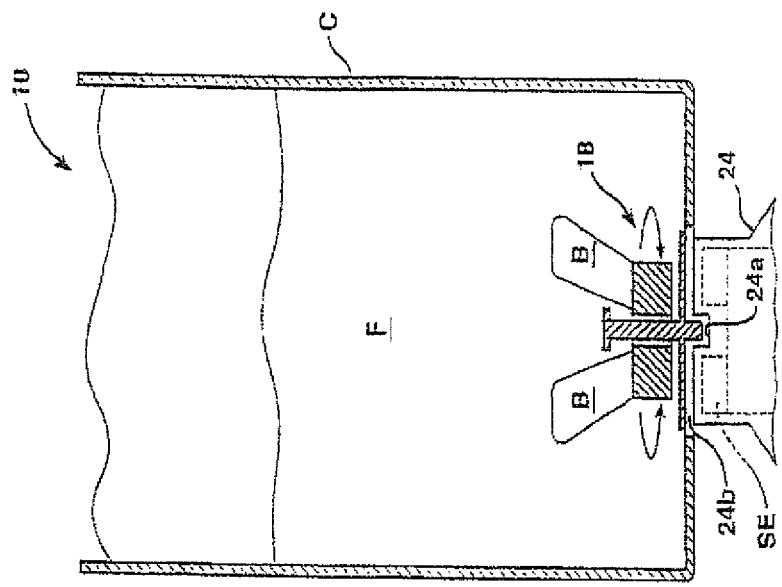
FIG. 2 is a partially schematic, partially cross-sectional side view showing the vessel of FIG. 1 positioned in a rigid vessel, with the fluid-agitating element aligned with and levitated/rotated by an adjacent motive device.

An external motive device 24 is then used to cause the fluid-agitating element 18 (which is at least partially magnetic or ferromagnetic) to at least rotate to agitate any fluid F in the bag 10. In the embodiment of FIG. 2, the fluid-agitating element 18 is at least partially magnetic and is shown as being levitated by the motive device 24, which is optional but desirable. As described in my U.S. Pat. No. 6,758,593, the disclosure of which is incorporated herein by reference, the levitation may be provided by a field-cooled, thermally isolated superconducting element SE (shown in phantom in FIG. 2) positioned within the motive device 24 and thermally linked to a cooling source (not shown). As also described therein, the fluid-agitating element 18 may then be rotated by rotating the superconducting element SE (in which case the fluid-agitating element 18 should produce an asymmetric magnetic field, such as by using at least two spaced magnets having alternating polarities). Another option is to use a separate drive structure (e.g., an electromagnetic coil) to form a coupling capable of transmitting torque to the particular fluid-agitating element (which may be "levitated" by a hydrodynamic bearing; see, e.g., U.S. Pat. No. 5,141,327 to Shiobara). While it is of course desirable to eliminate the need for a dynamic seal or opening in the bag through which a drive structure (such as a shaft) extends, the particular means used to levitate and/or rotate the fluid-agitating element 18 is not considered critical to practicing the inventions disclosed herein.

The fluid-agitating element 18 is also depicted as including a plurality of vanes or blades B to improve the degree of fluid agitation. If present, the vanes or blades B preferably project in a direction opposite the corresponding surface of the rigid portion 14. The particular number, type, and form of the vanes or blades B is not considered important, as long as the desired degree of fluid agitation for the particular application is provided. Indeed, in applications where only gentle agitation is required, such as to prevent damage to delicate suspensions or to merely prevent stagnation of the fluid F in the bag 10, the vanes or blades B need not be provided, as a rotating smooth-walled annular element 18 still provides some degree of agitation.

As explained above, it may be desirable to not only know the general location or position of the fluid-agitating element 18 within the bag 10, but also to assure its position relative to the motive device 24. To do so, and in accordance with a second aspect of the invention, the rigid portion 14 may be provided with a second receiver 26 to facilitate the correct positioning of the motive device 24 relative to the fluid-agitating element 18 when held at the home location. In the embodiment shown in FIGS. 1a and 1b, the second receiver 26 takes the form of a second post 28 projecting in a direction opposite the first post 20. Preferably, the second post 28 is essentially coaxial with the first post 20 (although the post 20 may be a separate component that fits into a receiver 14a defined by the second post 28; see FIG. 1c) and is adapted to receive an opening 24a, such as a bore, in the adjacent end face 24b forming a part of the housing for the motive device 24. Consequently, the second post 28 helps to assure that the alignment between the fluid-agitating element 18 (which is generally held in the vicinity of the first receiver 16/post 20, which is the home location) and the motive device 24 is proper such that the desired coupling for transmitting the levitation or rotational force may be formed.

Preferably, the second receiver 26, such as second post 28, has a cross-sectional shape corresponding to the shape of the opening 24a. For example, the second post 28 may be square in cross-section for fitting in a correspondingly-shaped opening 24a or locator bore. Likewise, the second post 28 could have a triangular cross-sectional shape, in which case the opening 24a would be triangular. Myriad other shapes could also be used, as long as the shape of the second receiver 26 compliments that of the opening 24a such that it may be freely received therein. In this regard, it is noted that a system of matching receivers and openings may be used to ensure that the fluid-agitating element 18 in the bag 10 corresponds to a particular motive device 24. For example, in the case where the fluid-agitating element 18 includes a particular arrangement of magnets producing a magnetic field that corresponds to a particular superconducting element or drive structure, the second receiver 26 may be provided with a certain shape that corresponds only to the opening 24 in the motive device 24 having that type of superconducting element or drive structure. A similar result could also be achieved using the relative sizes of the second receiver 26 and the opening 24a, as well as by making the size of the opening 18a such that it only fits on a first receiver 16 having a smaller width or diameter, and then making the second receiver 26 correspond to an opening 24a in a motive device 24 corresponding to that element 18.

In many past arrangements where a rigid vessel is used with a fluid-agitating element directly supported by a bearing, an external structure is provided to which a motive device could be directly or indirectly attached and held in a suspended fashion (see, e.g., U.S. Pat. No. 4,209,259 to Rains et al., the disclosure of which is incorporated herein by reference). This structure serves to automatically align the motive device with the fluid-agitating element supported therein. However, a bag 10 per se is generally incapable of providing reliable support for the motive device 24, which can weigh as much as twenty kilograms. Thus, the motive device 24 in the embodiments disclosed herein for use with a vessel in the form of a bag 10 is generally supported from a stable support structure (not shown), such as the floor, a wheeled, height adjustable platform, or the like. Since there is thus no direct attachment with the bag 10, the function performed by the second receiver 26 in aligning this device with the fluid-agitating element 18 is an important one.

Another embodiment of the vessel forming one aspect of the present invention is shown in FIGS. 3a and 3b. In this embodiment, the vessel is again a bag 10 including a flexible portion 12 and a rigid portion 14. The rigid portion 14 is cap or hat-shaped with a peripheral flange 22 for attachment to the flexible portion 12 of the bag 10. The connection between the two structures may be formed using the various techniques described above, and preferably results in a fluid-impervious, hermetic seal. The rigid portion 14 includes a first receiver 16 in the form of a recess or cavity 30 facing the interior of the bag (see action arrow B) for receiving a correspondingly-shaped portion of the fluid-agitating element 18 in the bag 10 and holding it at a home location, at least when oriented as shown in FIG. 3a. The portion of the fluid-agitating element 18 received in the cavity 30 is preferably the body 18b, which as described above is at least partially magnetic or ferromagnetic and may optionally support a plurality of vanes or blades B. Preferably, the body 18b of the fluid-agitating element 18 is circular in cross-section and the cavity 30 is sized and shaped such that the body (which need not include opening 18a in view of the absence of post 20) may freely be inserted, rotate, and levitate therein. However, as with the first embodiment, the fluid-agitating element 18 could also be in the form of a conventional magnetic stirrer (which of course would not be levitated), such as a bar having a major dimension less than the corresponding dimension (e.g., the diameter) of the cavity 30. In any case, the fluid-agitating element 18 in this embodiment is again free of direct attachment from the first receiver 16, but is held at a home location, even in the event decoupling.

Thus, in the manner similar to that described above with respect to the first embodiment, the fluid-agitating element 18 may be positioned in the first receiver 16 in the bag 10. The bag 10 may then be sealed, folded for storage or shipping, stored or shipped, and ultimately unfolded for use. The folding is preferably completed such that the fluid-agitating element 18 is captured in the cavity 30 and remains held in place during shipping by an adjacent portion of the bag 10. Consequently, upon unfolding the bag 10, the fluid-agitating element 18 is at the expected or home location, but remains free of direct attachment and ready to be rotated (and possibly levitated). If levitated, the levitation height established by the superconducting bearing or hydrodynamic bearing is preferably such that at least a portion of the body 18b of the fluid-agitating element 18 remains within the confines of the cavity 30. This helps to assure that the fluid-agitating element 18 remains held at the home location (that is, in the vicinity of the first receiver 16), even in the case of accidental decoupling from the motive device 24. In other words, in the event of an accidental decoupling, the fluid-agitating element 18 will engage the sidewall of the cavity 30 and simply come to rest therein, which defines the home location. This not only improves the chance of an automatic recoupling, but also makes the task of manually reforming the coupling an easy one.

An option to assure that a magnetic fluid-agitating element 18 remains associated with the first receiver 16, even if inverted, is to attach an attractive structure, such as a magnet 32 (shown in phantom in FIG. 3a), to the exterior of the rigid portion 14. The non-contact coupling thus established helps ensure that the fluid-agitating element 18 remains in the home location prior to being coupled to an external motive device. The magnet 32 is removed once the bag 10 is positioned on or in a support structure, such as a container C (see FIG. 2). Such a magnet 32 may also be used with the embodiment of FIG. 1, which eliminates the need for providing the post 20 with portion 20a. The magnet 32 is preferably annular with an opening that is received by the second receiver 26, which advantageously helps to ensure the proper alignment for forming the coupling.

Yet another option is to provide a frangible adhesive on the fluid-agitating element 18 to hold it in place temporarily in the first receiver 16 prior to use. The strength of any adhesive used is preferably such that the bond is easily broken when the fluid-agitating element 18 is levitated in the first receiver 16. Of course, the use of such an adhesive might not be possible in situations where strict regulations govern the purity of the fluid being mixed.

With reference to FIG. 3b, the first receiver 16 in this embodiment also serves the dual function of helping to align the fluid-agitating element 18 relative to an external motive device 24. Specifically, the periphery of the sidewall 34 and the end wall 36 defining the cavity 30 in the rigid portion 14 define a second receiver 26 adapted to receive an opening 24a formed in an adjacent face of a motive device 24. As described above, the opening 24a is preferably sized and shaped for being received by the second receiver 26, and may even help to ensure that the bag 10 is used only with a motive device 24 having the correct superconducting element or magnetic structure(s) for levitating and/or rotating the fluid-agitating element 18. For example, in the case where the sidewall 34 and end wall 36 provide the second receiver 26 with a generally cylindrical shape, the opening 24a is also cylindrical. Preferably, the opening 24a also has a depth such that the end wall 36 rests on the corresponding face 24c of the motive device 24. This feature may be important to ensure that the gap between the superconducting element and/or drive structure in the motive device 24 and the at least partially magnetic or ferromagnetic body 18b of the fluid-agitating element 18 is minimized, which helps to ensure that the strongest possible coupling is established and that the maximum amount of driving torque is transferred. The gaps are shown as being oversized in FIG. 3b merely to provide a clear depiction of the relative interaction of the structures shown. However, in the case where the entire housing of the motive device 24 is rotated, it may be desirable to provide a certain amount of spacing between the sidewall 34, the end wall 36, and the corresponding surfaces defining the opening 24a to avoid creating any interference.

Figure 4B:
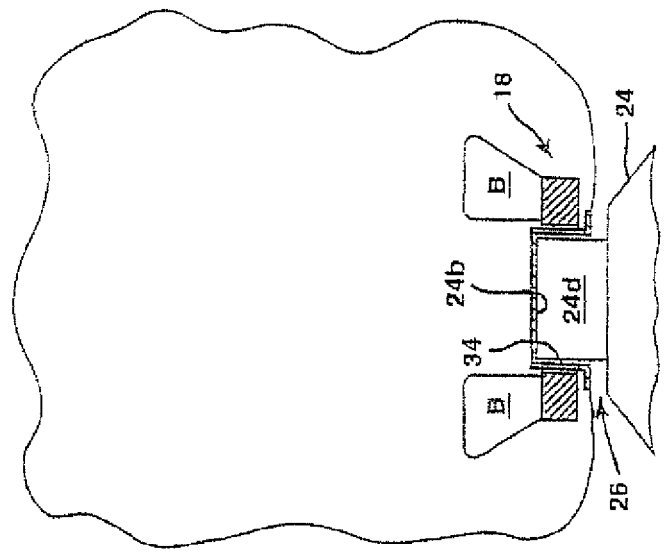
Figure 4A:
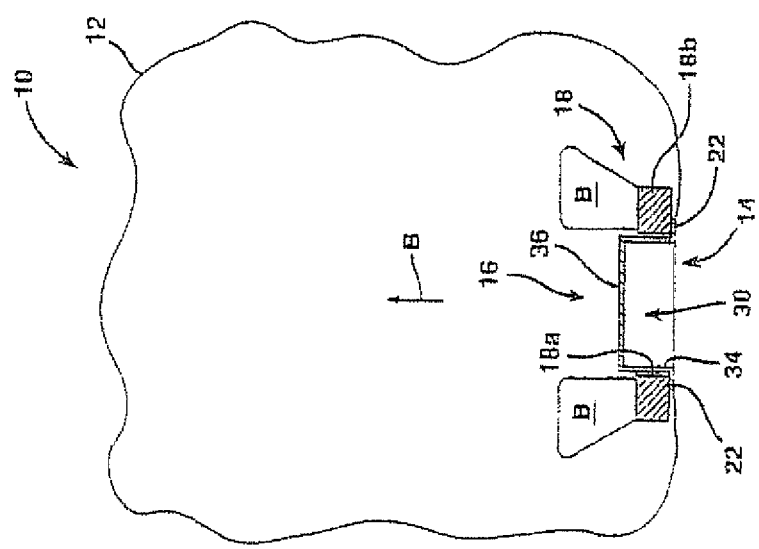
FIG. 4a is partially schematic, partially cross-sectional side view showing another embodiment of the vessel, including a hat or cap-shaped rigid portion having a cavity facing outwardly.

FIGS. 4a and 4b show an embodiment similar in some respects to the one shown in FIGS. 3a and 3b. For example, the rigid portion 14 includes a peripheral flange 22 connected to the flexible portion 12 of the bag 10 to form a seal. Also, the rigid portion 14 includes a sidewall 34 and end wall 36 that together define a cavity 30. However, a major difference is that the cavity 30 of the rigid portion 14 essentially faces outwardly, or toward the exterior of the bag 10 (e.g., in a direction opposite action arrow B). Consequently, the sidewall 34 and end wall 36 define the first receiver 16 for receiving the fluid-agitating element 18, which is shown having an annular body 18b that is at least partially magnetic or ferromagnetic and may support a plurality of vanes or blades B. As should be appreciated, the first receiver 16 in the form of the periphery of the sidewall 34 provides a similar receiving function as both the post 20 and the cavity 30 of the other embodiments, since it is capable of maintaining, holding, or confining the fluid-agitating element 18 substantially in a home or expected position within the bag 10. The maximum amount of side-to-side movement is of course dependent on the size of the opening 18a in the fluid-agitating element.

Additionally, the outwardly-facing cavity 30 is adapted to serve as the second receiver 26 for receiving a portion of a motive device 24 used to levitate and rotate the fluid-agitating element 18 and serving to align the two. Specifically, the motive device 24 may include a head end 24d adapted for insertion in the cavity 30 to form the desired coupling with the fluid-agitating element 18 positioned adjacent thereto. As with the embodiments described above, the spacing between the head end 24d and at least the sidewall 34 is preferably minimized to maximize the strength of the coupling between the motive device 24 and the fluid-agitating element 18. Moreover, in view of the rigid nature of the rigid portion 14, the end face 24b of the head end 24d may rest against and assist in supporting the bag 10 (which, as described above, may be positioned in a separate, semi-rigid container (not shown)).

In each of the above-referenced embodiments, the possible use of a levitating fluid-agitating element 18 with a superconducting bearing or a hydrodynamic bearing is described. In such systems, a real possibility exists that the fluid-agitating element 18 might accidentally decouple or disconnect from the motive device 24, such as if the fluid is viscous or the amount of torque transmitted exceeds the strength of the coupling. In a conventional bag, the process of reestablishing the coupling is extraordinarily difficult, since the location of the fluid-agitating element 18 within the bag 10 is unknown. In a sterile environment, opening the bag 10 and using an implement to reposition or "fish" out the fluid-agitating element 18 is simply not an option. Thus, an added advantage of the use of the first receiver 16 in each of the above-referenced embodiments is that, despite being free from direct attachment, it still serves the function of holding the fluid-agitating element 18 at the home location in instances where accidental decoupling occurs. This significantly reduces the downtime associated with such an event, since the general position of the fluid-agitating element 18 is known. The use of a first receiver in the bag 10 also improves the chances of automatic recoupling, since the fluid-agitating element 18 remains generally centered relative to the motive device 24 and held generally at the home location, even when decoupling occurs.

A related advantage is provided by forming the first receiver 16 in or on a rigid portion 14 of the bag 10. Specifically, in the case where a fluid-agitating element rests on a surface of a bag, the contact over time could result in damage and could even lead to an accidental perforation, which is deleterious for obvious reasons. The possibility for such damage or perforation also exists when a levitating fluid-agitating element 18 accidentally decouples. Advantageously, the potential for such damage or perforation is substantially eliminated in the foregoing embodiments, since the first receiver 16 helps to keep the fluid-agitating element 18 adjacent to the flange 22 of the rigid portion 14, which is generally thicker and less susceptible to being damaged or perforated. In other words, if the fluid-agitating element 18 becomes decoupled, it only engages or contacts the rigid portion 14 of the bag 10. Thus, it is preferable for the flange 22 to be oversized relative to the fluid-agitating element 18. While the embodiments of FIGS. 1-4 are described as bags 10 including both a flexible portion 12 and a rigid portion 14, it should be appreciated that the present invention extends to a completely rigid vessel (that is, one made of metal, glass, rigid plastics, or the like). In the case of a rigid vessel, the post 20 preferably includes a portion 20a for capturing the fluid-agitating element 18 thereon, but without any other means of direct attachment or bearing.

Up to this point, the focus has been on a fluid-agitating element 18 capable of levitating in the vessel. However, as briefly noted above, the inventions described herein may also be applied to a bag 10 in combination with a fluid-agitating element 18 directly supported by one or more bearings. For example, as shown in FIGS. 5a and 5b, the first receiver 16 associated with the rigid portion 14 of the bag 10 may be in the form of an inwardly-projecting post 20 including a slide bearing 40 for providing direct support for the fluid-agitating element 18. The bearing 40 is preferably sized and shaped such that it fits into an opening 18a forming in the fluid-agitating element 18, which may rest on the adjacent surface of the post 20 or may be elevated slightly above it. In either case, it should be appreciated that the first receiver 16 receives and holds the fluid-agitating element 18 in a home location, both during shipping and later use.

In view of the direct nature of the support, the material forming the slide bearing 40 is preferably highly wear-resistant with good tribological characteristics. The use of a slide bearing 40 is preferred in applications where the bag 10 is disposable and is merely discarded, since it is less expensive than a corresponding type of mechanical roller bearing (and is actually preferred even in the case where the bag 10 is reused, since it is easier to clean). However, it is within the broadest aspects of the invention to provide the first receiver 16 with a conventional roller bearing for providing direct, low-friction, rolling support for the rotating fluid-agitating element 18, although this increases the manufacturing expense and may not be acceptable in certain applications.

The rigid portion 14 of the bag 10 in this embodiment may further include a second receiver 26 in the form of a second post 28 coextensive and coaxial with the first post 20. The second post 28 is received in an opening 24a formed in an end face 24b of a motive device 24. In view of the direct support provided for the fluid-agitating element 18 by the bearing 40, the motive device 24 in this case includes only a drive structure DS (shown in phantom in FIG. 5b) for forming a coupling with the body 18b, which is magnetic or ferromagnetic (iron, magnetic steel, etc.). The drive structure DS may be a permanent magnet or may be ferromagnetic, as necessary for forming the coupling with the fluid-agitating element 18, which may be disc-shaped, cross-shaped, an elongated bar, or have any other suitable shape. The drive structure DS may be rotated by a direct connection with a motor (not shown), such as a variable speed electric motor, to induce rotation in the fluid-agitating element 18. Alternatively, the drive structure DS may be an electromagnet with windings to which current is supplied to cause the magnetic fluid-agitating element 18 rotate and possibly levitate slightly to create a hydrodynamic bearing (see, e.g., U.S. Pat. No. 5,141,327, the disclosure of which is incorporated herein by reference). Again, it is reiterated that the particular type of motive device 24 employed is not considered critical to the present invention.

Figure 6A:
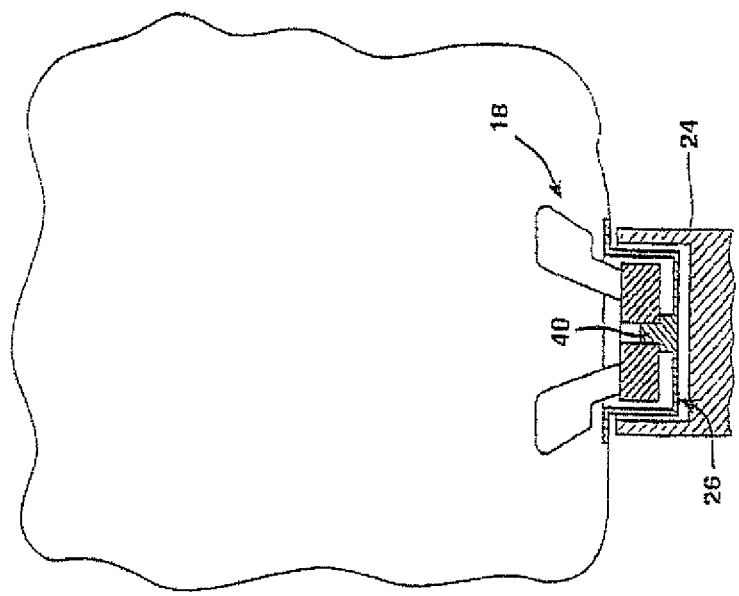
Figure 6B:
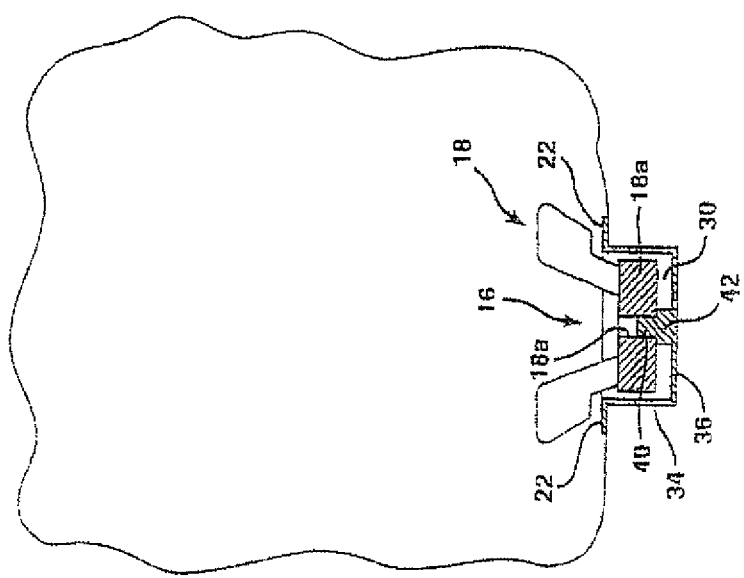

FIGS. 6a and 6b show an embodiment of the bag 10 in which the first receiver 16 is in the form of a cavity 30 formed in the rigid portion 14 and facing inwardly. A bearing 40 is provided in the cavity 30 for providing direct support for a fluid-agitating element 18 positioned therein. As with the embodiment described immediately above, the bearing 40 may be a slide bearing adapted for insertion in the opening 18a of the fluid-agitating element 18 formed on the head end of a post 42. The post 42 may be supported by or unitarily formed with the end wall 36. Despite the depiction of a slide bearing 40, it is reiterated that the particular type of bearing used is not considered critical, as long as rotational support is provided for the fluid-agitating element 18 and the other needs of the particular fluid-agitating operation are met (e.g., low friction, reduced expense, easy clean-up).

The body 18b of the fluid-agitating element 18, which is at least partially magnetic or ferromagnetic, is sized to fit within the sidewall 34 defining the cavity 30 and, thus, is capable of rotating therein as the result of an externally-applied, non-contact motive force. The periphery of the sidewall 34 also defines a second receiver 26 for receiving a corresponding opening 24a in a motive device 24, which in view of the direct support provided by bearing 40 need only provide the force necessary to rotate the fluid-agitating element 18 in a non-contact fashion.

Figure 7A:
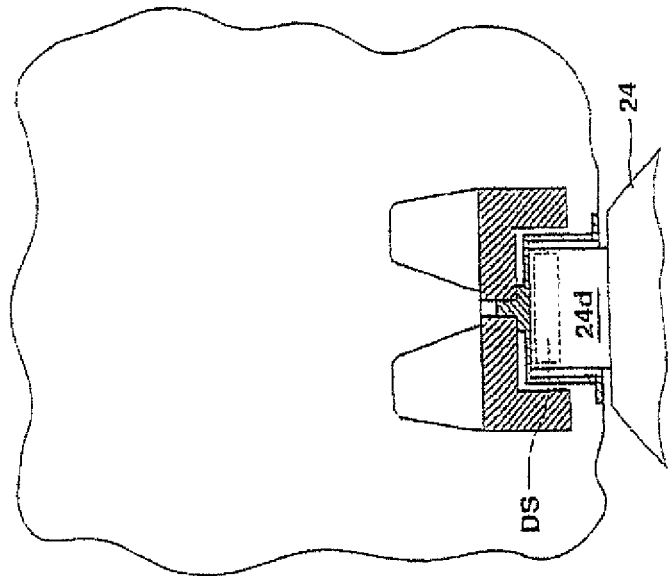
Figure 7B:
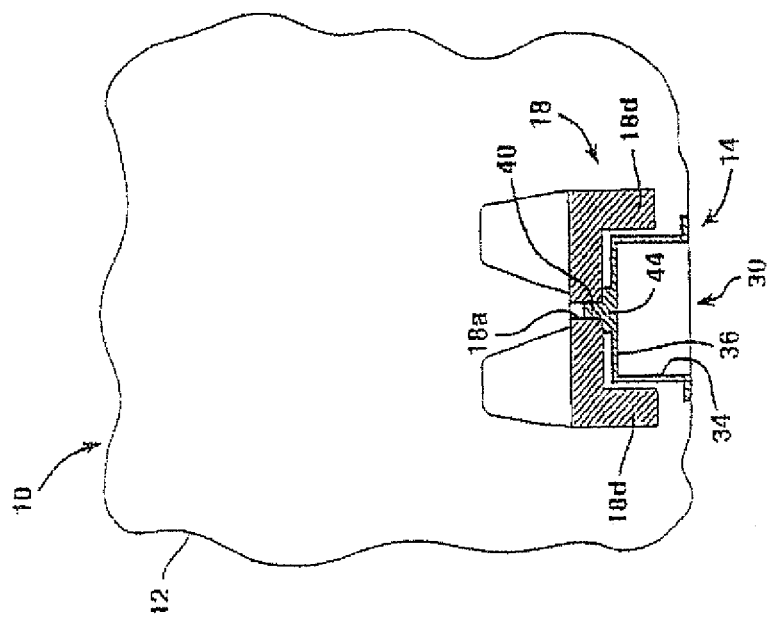

As should be appreciated, the embodiment shown in FIGS. 7a and 7b is the direct support counterpart for the embodiment shown in FIGS. 4a and 4b. The rigid portion 14 again includes a cavity 30 facing outwardly or toward the exterior of the bag 10 and a first receiver 16 for receiving and defining a home location for a fluid-agitating element 18. The first receiver 16 includes a bearing 40 for supporting the fluid-agitating element 18, which again is at least partially magnetic or ferromagnetic. The bearing 40 may be a slide bearing formed on the head end of a post 44 integral with the end wall 36 of the rigid portion 14 and adapted for fitting into an opening or recess 18a in the fluid-agitating element 18, or may be a different type of bearing for providing support therefor.

The motive device 24 includes a head end 24d adapted for insertion in a second receiver 26 defined by the cavity 30. This head end 24d preferably includes the drive structure DS that provides the force for causing the at least partially magnetic or ferromagnetic fluid-agitating element 18 to rotate about bearing 40. In FIGS. 7a and 7b, it is noted that the fluid-agitating element 18 includes an optional depending portion 18d that extends over the sidewall 34. As should be appreciated, this portion may also be magnetized or ferromagnetic such that a coupling is formed with the drive structure DS. A similar type of fluid-agitating element 18 could also be used in the levitation scheme of FIGS. 4a and 4b.

Figure 8:
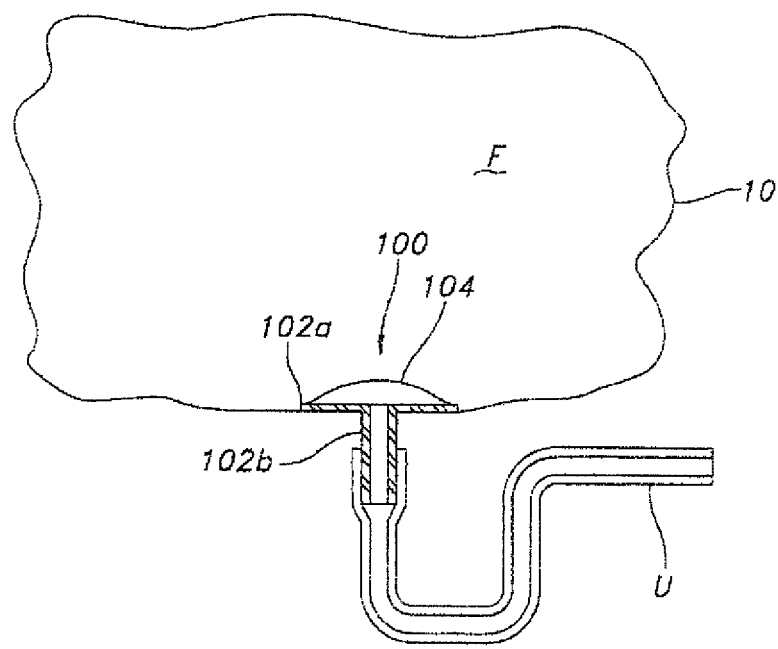
FIG. 8 schematically illustrates one possible embodiment of an integral sparger.

Turning now to FIG. 8, and as noted in the foregoing description, it may also be desirable to provide the bag 10 with an integral sparger 100 including means for forming bubbles in the fluid. In the illustrated embodiment, the sparger 100 includes a face portion 102a for attaching to the bag 10 and a tubular projecting portion 102b for coupling with an external source of gas, such as through a tube U. The face portion 102a may comprise a disk-shaped piece of rigid plastic material, and may be welded directly to the flexible material forming the bag 10 adjacent the fluid F when present such that a fluid-impervious seal results.

Gas introduced through the tube U from a remote source (not shown) thus enters the bag 10, passing through any fluid present. In the illustrated embodiment, the means for forming bubbles in the gas entering the fluid comprises a perforated piece of plastic film 104 may also be secured adjacent the face portion 102a of the sparger 100, such as by welding. To create the small bubbles desired for many bioprocessing applications, the holes in the film 104 are preferably in the sub-millimeter range. Alternatively, a porous film may be used, various types of which are generally well known in the art (see, e.g., U.S. Pat. No. 4,814,124, incorporated herein by reference). In either case, the bag 10 with the integral sparger 100 may simply be disposed upon recovering all or part of the fluid, or alternatively a product therefrom.

Figure 9:
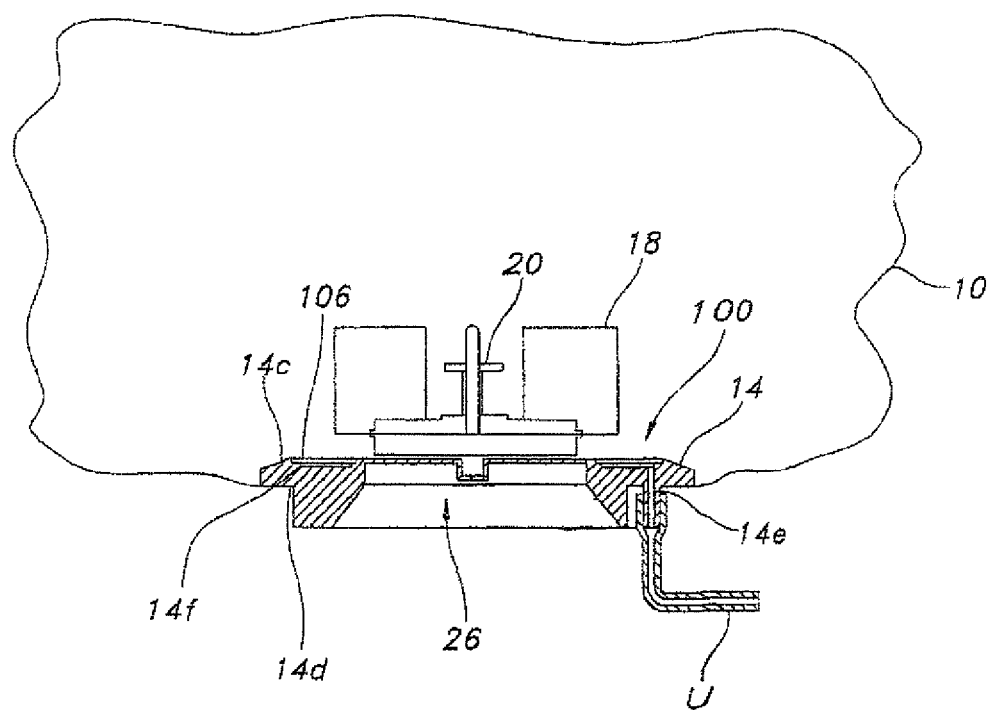
FIG. 9 schematically illustrates another possible embodiment of an integral sparger.

Instead of providing a separate sparger 100, it is also possible to combine it with the rigid portion 14 of the bag 10 for receiving the fluid-agitating element 18 and providing the desired centering/alignment function. Thus, as shown in FIG. 9, the rigid portion 14 is welded to the bag 10, as described above, preferably along the bottom and such that a fluid-impervious seal is formed. A receiver in the form of a post 20 may be removably attached to the rigid portion 14 through the opening (not shown) in the fluid-agitating element 18 (such as by providing a threaded bore in the rigid portion for receiving a threaded end of the post, or as shown in FIG. 1c, a bore 14a having a groove for establishing a snap-fit engagement with the post), and may include an oversized head for providing a retaining function. As described above, a second receiver 26 in the form of a recess or cavity in the rigid portion 14 may also be provided for receiving an external motive device, such as a rotating drive magnet or superconducting element (not shown).

The face 14c of the rigid portion 14 further includes a first passage 14d in communication with both the interior of the bag 10 and a second passage 14e leading to an external source of gas via a tube U. Gas introduced through the tube U thus exits into the interior of the bag 10 through the first passage 14d, which may be associated with a perforated piece of material 106 comprising the means for forming the bubbles. In the preferred embodiment, the first passage 14d is annular and includes seating ledges 14f for receiving the material 106, which takes the form of an annular piece of plastic film having a plurality of holes or apertures to form the perforations (which, again, are preferably sized in the sub-millimeter range) that is welded in place. Advantageously, the sparger 100 thus created in the illustrated embodiment releases the bubbles in close proximity to the fluid-agitating element 18, thus enhancing their dispersion throughout the fluid.

Figure 10A:
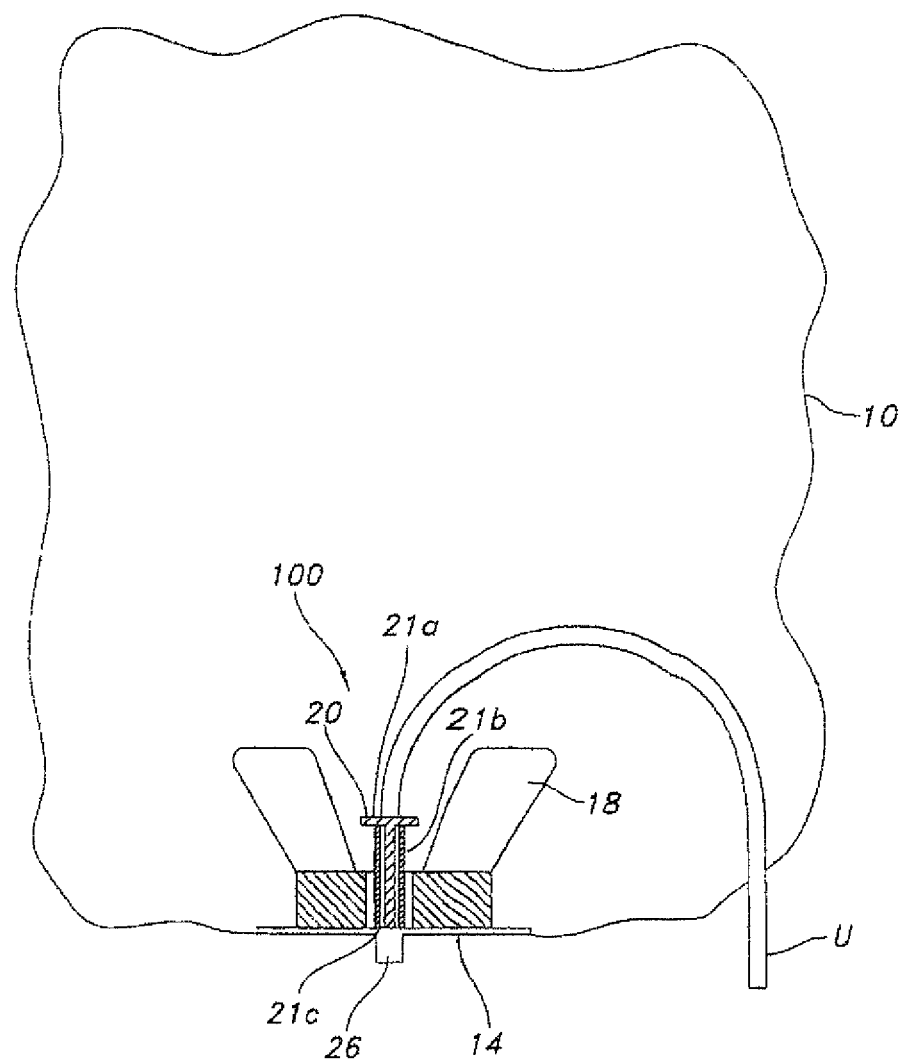
FIGS. 10a and 10b show yet another possible embodiment of an integral sparger.
Figure 10B:
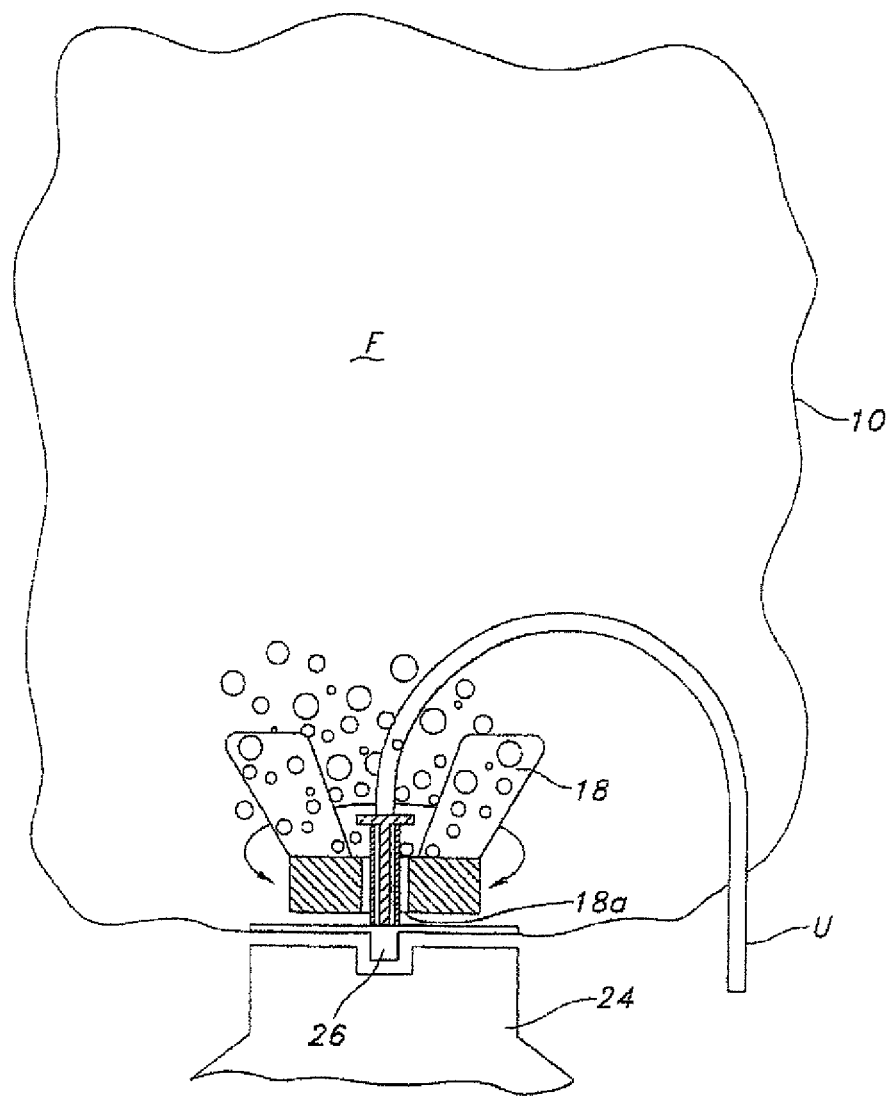

In yet another, but similar embodiment shown in FIGS. 10a and 10b, the sparger 100 is integral with the rigid portion 14 connected to the bag 10, which may again include a receiver in the form of an inwardly projecting post 20 for receiving the fluid-agitating element 18 and an outwardly directed alignment structure 26. The post 20 in this embodiment includes an inlet 21a for connecting with a tube U coupled to an external source of gas (not shown), such as through an opening or open end of the bag, and an outer wall 21b formed of a perforated or gas permeable material that serves as the means for forming bubbles in this embodiment. To add rigidity to the post 20, a center support 21c may also be provided concentric with the outer wall 20b.

Thus, gas passing through the tube U exits the outer wall 20b of the post 20 as bubbles (the size of which depend on the size of the perforations made, which again are preferably in the sub-millimeter range). As shown in FIG. 10b, when the fluid-agitating element 18 is levitated and/or rotated by an adjacent, but external motive device 24, the bubbles are released adjacent the opening 18a and dispersed throughout the fluid F. Once use of the bag 10 is complete, it may then simply be discarded along with the sparger 100.

Figure 11:
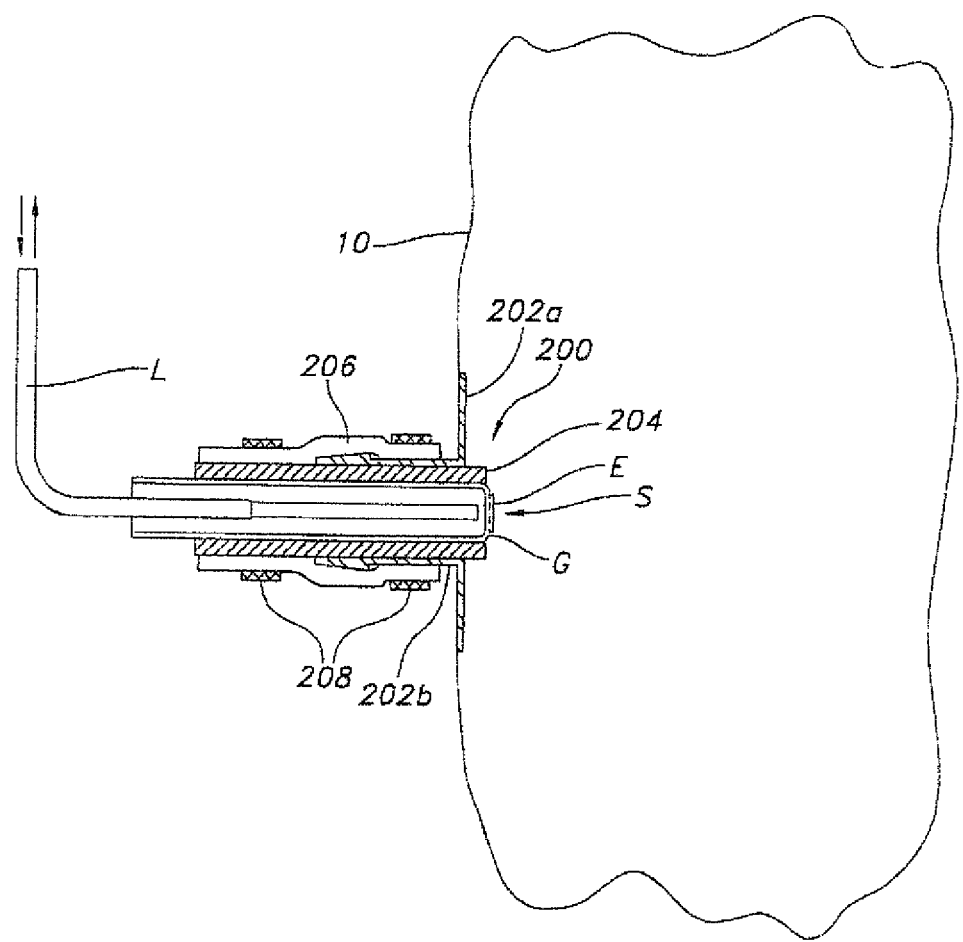
FIG. 11 illustrates an embodiment of a bag including a sensor receiver.

Besides a sparger 100 and/or a magnetic fluid-agitating element 18, it may also be desirable to provide disposable means in the bag 10 to facilitate sensing characteristics of the fluid, such as the pH, oxygen content, temperature. etc. Thus, in the embodiment of FIG. 11, the bag includes a rigid receiver 200 for receiving a sensor S. In the illustrated embodiment, a translucent or transparent (preferably glass), close-ended tube G receives a fiber optic cable L for transmitting light to and receiving back the reflected light (note bidirectional arrows). The receiver 200 includes a face 202a having a periphery to which the bag 10 is attached, such as by welding, to form a fluid impervious seal. A tubular portion 202b of the receiver 200 receives a bushing 204, which in turn receives the closed end of the transparent tube G and allows it to pass into contact with the fluid F when present in the bag 10. A sealing tube 206, preferably made of flexible plastic or an elastic material, couples the bushing 204 to the tubular portion 202b of the receiver 200 (which may include a slightly oversized, frusto-conical portion defining a hold-assist ledge for the tube). Fasteners, such as cable ties 208, may help to removably secure the sealing tube 206 in place, although other means for sealing could be used instead, such as adhesives or the like. The important point is that no appreciable amount of fluid can pass the tube G once inserted. in the receiver 200.

The tube G may carry a sensor S in the form of a fluorescent sensing element E, preferably by way of external attachment to the closed, transparent or translucent end (which thus forms a window for allowing light to be transmitted to the sensing element). As is known in the art, this element E may change its fluorescence characteristics in response to change in the pH, dissolved oxygen, carbon dioxide, or temperature of the fluid it is touching. The fluorescence characteristics can then be measured by external apparatus capable of illuminating the sensitive element E, such as through the cable L, and the transparent closed end of the tube G. As should be appreciated, this type of sensitive element E is not only disposable, but also advantageously does not require any power or leads. As a result of this arrangement, the above mentioned parameters of the fluid can be measured non-invasively, and the tube G simply discarded along with the bag 10 when the bioprocessing operation is complete. The receiver 200 may thus be considered to form an optical port with a sensitive element E attached to an inner surface of an optical window. An example of an off-the-shelf sensor element E is one manufactured by PreSens (or Precision Sensing) GmbH Josef-Entert-Str. 9 D-93053 Regensburg Germany.

Obvious modifications or variations are possible in light of the above teachings. For example, instead of forming the rigid portion 14 as part of the bag 10 by forming a seal at an interface between the two, it could also be positioned in contact to an inner or outer surface of the bag and attached using vacuum-forming techniques, adhesives, or the like. For example, in the cap-shaped embodiment of FIG. 3a, the bag 10 would essentially line the inside surfaces of the sidewall 34 and end wall 36. Likewise, in the embodiment of FIG. 4a, the bag 10 would cover the sidewall 34 and end wall 36. In both cases, the need for the flange 22 may be eliminated. It is also possible to provide any of the first receivers with a tapered or frusto-conical engagement surface that mates with a corresponding surface on the fluid-agitating element, as disclosed in my co-pending patent application Ser. No. PCT/US01/31459, the disclosure of which is incorporated herein by reference. The integral sparger 14 may also be provided in the embodiment in which the rigid portion 14 is cap or cup-shaped, such as by providing the perforated/permeable material (whether film, rigid, or otherwise) for forming the bubbles along the peripheral flange 22, sidewall 34, or end wall 36, and providing a passage to allow for gas to communicate with it from a remote source (such as through an external tube).

The foregoing descriptions of various embodiments of the present inventions have been presented for purposes of illustration and description. These descriptions are not intended to be exhaustive or to limit the invention to the precise forms disclosed. The embodiments described provide the best illustration of the principles of the invention and its practical applications to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. A port for use with a bioreactor vessel, said port comprising:
- a base member comprising a hollow portion and a base plate for sealing to the wall of the bioreactor vessel;
- a hollow, partially transparent member for containing monitoring components, which member fits inside the bore of the hollow portion of said base member, said transparent member providing access to the contents of said bioreactor vessel;
- a monitoring assembly inserted into said member, which assembly comprises means for providing incoming signals and means for collecting and transmitting measurement signals resulting from the interaction of said incoming signals with the contents of said bioreactor vessel; and
- a fastener to maintain the position and alignment of the monitoring assembly.

2. The port of claim 1, wherein said monitoring assembly measuring at least one of temperature, pH, and/or the oxygen content in said bioreactor vessel.

3. The port of claim 1, wherein said fastener at least partially covers the monitoring assembly and maintains the position of said monitoring assembly relative to said base member.

4. The port of claim 1, wherein said monitoring assembly components are optical.

5. The port of claim 1, wherein the means for providing incoming signals comprises an external apparatus capable of producing light.

6. The port of claim 1, wherein the means for collecting and transmitting measurement signals resulting from the interaction of the signals with the contents comprises a cable.

7. A port for use with a bioprocessing vessel, comprising:
- a receiver for connecting to the vessel, said receiver including a hollow portion;
- an at least partially transparent member supported by the receiver;
- a sensor adapted for communicating with the contents of the vessel through the partially transparent member; and
- a fastener for maintaining the position and alignment of the sensor relative to the vessel.

8. The port of claim 7, wherein the transparent member includes a sensor element arranged to contact the contents of the vessel.

9. The port of claim 8, wherein the transparent member comprises a generally hollow member having at least a transparent end including the sensor element.

10. The port of claim 7, wherein a sensor element is arranged for contacting the contents of the vessel.

11. The port of claim 10, wherein the sensor element is supported by the receiver.

12. The port of claim 10, wherein the sensor element is adapted for sensing at least one of temperature, pH, and/or the oxygen content in the vessel.

13. The port of claim 7, wherein the sensor is adapted for providing incoming signals and for collecting and transmitting measurement signals resulting from the interaction of the incoming signals with the contents of the vessel.

14. An apparatus for use in connection with processing a fluid in the course of a bioprocessing operation, comprising:
- a vessel for receiving the fluid, the vessel having a flexible wall at least partially defining an interior compartment, a portion of the vessel formed by the flexible wall having no predetermined shape and capable of assuming a shape based on the presence of the fluid in the interior compartment;
- a receiver for connecting to the vessel, said receiver including a hollow portion;
- a sensor assembly for non-invasively sensing a characteristic of the fluid, the sensor assembly adapted for insertion in the receiver to provide incoming signals and for collecting and transmitting measurement signals resulting from the interaction of the incoming signals with the contents of the vessel; and
- a fastener for maintaining the position and alignment of the sensor assembly relative to the vessel.

15. The apparatus of claim 14, wherein the receiver includes a transparent portion for positioning in optical communication with the contents of the vessel, and further including a sensor element associated with the transparent portion and configured for contacting the contents of the vessel.

16. The apparatus of claim 14, wherein the fastener is external to the vessel.

17. The apparatus of claim 14, wherein the fastener does not contact the fluid in the vessel.

18. A flexible bag for forming the bioprocessing vessel and including the apparatus of claim 1.

19. A flexible bag for forming the bioprocessing vessel and including the apparatus of claim 7.

20. The apparatus of claim 7, wherein the transparent member includes a sensor element.

21. The apparatus of claim 14, wherein the vessel comprises a flexible bag.

22. The apparatus of claim 21, wherein a portion of the receiver is external to the bag.

23. The apparatus of claim 21, wherein a portion of the receiver projects outwardly from the wall of the bag.

24. The apparatus of claim 21, wherein the receiver is welded to the wall of the bag.

25. The apparatus of claim 21, wherein the receiver includes a face having a periphery attached to the bag.

26. The apparatus of claim 21, wherein the sensor assembly is adapted for providing incoming signals and for collecting and transmitting measurement signals resulting from the interaction of the incoming signals with the contents of the bag.

* * * * *